United States Patent [19]

Capps

[11] Patent Number: 4,626,540

[45] Date of Patent: Dec. 2, 1986

[54] SUBSTITUTED 1-AMINO-4-NITRO-ACRIDINONES AND METHODS OF TREATING BACTERIAL INFECTIONS AND LEUKEMIA WITH THEM

[75] Inventor: David B. Capps, Ann Arbor, Mich.

[73] Assignee: Warner-Lambert Company, Morris Plains, N.J.

[21] Appl. No.: 658,100

[22] Filed: Oct. 10, 1984

Related U.S. Application Data

[63] Continuation-in-part of Ser. No. 549,709, Nov. 8, 1983, abandoned.

[51] Int. Cl.$^4$ .................. A61K 31/47; C07D 219/08
[52] U.S. Cl. .................................. 514/297; 546/103
[58] Field of Search ..................... 514/297; 546/103

[56] References Cited

U.S. PATENT DOCUMENTS

| | | | |
|---|---|---|---|
| 2,647,901 | 8/1953 | Archer | 546/103 |
| 3,975,150 | 8/1976 | Brack | 546/103 X |
| 4,150,231 | 4/1979 | Ledochowski et al. | 546/106 |

OTHER PUBLICATIONS

Blanz et al., J. Med. Chem., vol. 6, pp. 185–191 (1963).
Romanowski et al., Chemical Abstracts, vol. 88, 169927k (1978).
Albert, The Acridines, 2nd ed., St. Martin'S Press, New York (1966), pp. 434, 436, 438, 449.
Ledochowski et al., Chemical Abstracts, vol. 60, 14471c–14472a (1964).
Radzikowski et al., Chemical Abstracts, vol. 75, 74667t (1971).
Proc. Soc. Exptl. Biol. Med., 91, 282–285 (1956) Arnold et al.
Roczniki Chemii 51, (1947), pp. 2455–2461, Romanowski et al.
Antibiotics 5, pp. 275–279 (1979) Gniazdowski et al.
Helvetica Chimica Acta 55, #185, 1972, pp. 1948–1958, Burdecka et al.
Helvetica Chimica Acta 58, #12–13, 1975, pp. 110–115, Manukian et al.

*Primary Examiner*—Robert Gerstl
*Assistant Examiner*—Diana G. Rivers
*Attorney, Agent, or Firm*—Ronald A. Daignault

[57] ABSTRACT

Substituted 1-amino-4-nitroacridinones, their method of manufacture, pharmaceutical compositions and their use as antibacterial and antitumor agents are herein described.

16 Claims, No Drawings

SUBSTITUTED 1-AMINO-4-NITRO-ACRIDINONES AND METHODS OF TREATING BACTERIAL INFECTIONS AND LEUKEMIA WITH THEM

CROSS-REFERENCE TO RELATED APPLICATION

This is a continuation-in-part of Ser. No. 549,709 filed Nov. 8, 1983, now abandoned.

BACKGROUND OF THE INVENTION

1-Alkylaminoalkylaminoacridones have been reported as possible antischistosomal agents but inactive in antitumor tests; see, for example, U.S. Pat. No. 2,647,901, Proc. Soc. Exptl. Biol. Med. 91, 282 (1956) and J. Med. Chem. 6, 185 (1964). The synthesis of 1-substituted amino-4-nitroacridones by reaction of 1-chloro-4-nitroacridone with aliphatic monoamines and amino acids has been described in Roczniki Chemii 51, 2455 (1977).

Antitumor activity has been disclosed for compounds of different chemical structure than the above, such as the compound of the formula

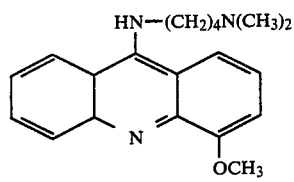

in Chem. Abstr. 60, 14471 (1964). Also described as potential anticancer agents in the same reference are 10-substituted-aminoalkylacridones such as, for example, a compound of the formula

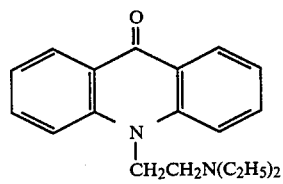

Nitracrine, a basically substituted nitroacridine, is being studied as an anticancer agent as reported in Antibiotics 5, 275 (1979).

SUMMARY OF THE INVENTION

The present invention relates to a compound of the formula

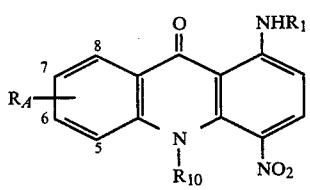

I where $R_1$ is alkylene-$NR_xR_y$ where alkylene is a 2 to 4 carbon straight or branched hydrocarbon chain and $R_x$ is hydrogen or $R_x$ and $R_y$ are each independently 1 to 4 carbon straight or branched chain alkyl, or 2 to 4 carbon straight or branched chain hydroxyalkyl, or combined with said nitrogen represent piperidyl, or pyrrolidyl, or alkylene-$NR_xR_y$-oxide where alkylene is a 2 to 4 carbon straight or branched hydrocarbon chain, and $R_x$ and $R_y$ are each independently 1 to 4 carbon straight or branched chain alkyl, or combined with said nitrogen represent piperidyl or pyrrolidyl; $R_{10}$ is H or 1 to 4 carbon straight or branched chain alkyl; $R_A$ is H or one or two groups selected from hydroxy, chloro, 1 to 4 carbon alkoxy, 2 to 8 carbon straight or branched alkanoyloxy, 1 to 4 carbon straight or branched alkoxycarbonyloxy, benzyloxy, amino, and 1 to 4 carbon monoalkyl- or dialkylamino, or a pharmaceutically acceptable acid addition salt thereof.

The present invention includes a pharmaceutical composition comprising an effective amount of a compound of the formula I or a pharmaceutically acceptable acid addition salt thereof with a pharmaceutically acceptable carrier.

The present invention includes a method for treating microbial infections in a mammal which comprises administering an effective amount of a compound of the formula I or a pharmaceutically acceptable salt thereof in admixture with a pharmaceutically acceptable carrier, to a mammal in need thereof.

The present invention includes a method for treating leukemia in a mammal which comprises administering an effective amount of a compound of the formula I wherein $R_1$ is alkylene-$NR_xR_y$ where alkylene is a 2 to 4 carbon straight or branched hydrocarbon chain and $R_x$ is hydrogen or $R_x$ and $R_y$ are each independently 1 to 4 carbon straight or branched chain alkyl, 2 to 4 carbon straight or branched chain hydroxyalkyl, or combined with said nitrogen represent piperidyl, or pyrrolidyl; or alkylene-$NR_xR_y$N-oxide where alkylene is a 2 to 4 carbon straight or branched hydrocarbon chain, and $R_x$ and $R_y$ are each independently 1 to 4 carbon straight or branched chain alkyl, or combined with said nitrogen represent piperidyl or pyrrolidyl; $R_{10}$ is H, 1 to 4 carbon straight or branched chain alkyl, $R_A$ is H or one or two groups selected from hydroxy, chloro, 1 to 4 carbon alkoxy, benzyloxy, 2 to 8 straight or branched alkanoyloxy, 1 to 4 carbon straight or branched alkoxycarbonyloxy amino, and 1 to 4 carbon monoalkyl- or dialkylamino, or a pharmaceutically acceptable salt thereof in combination with a pharmaceutically acceptable carrier, to a mammal in need thereof.

The invention also includes a method for treating solid tumors in a mammal which comprises administering and effective amount of a compound of the formula II as defined above or a pharmaceutically acceptable salt thereof in combination with a pharmaceutically acceptable carrier, to a mammal in need thereof.

DETAILED DESCRIPTION

A preferred embodiment of the present invention is a compound of the formula I wherein $R_1$ is alkylene-$NR_xR_y$ where alkylene is a 2 to 4 carbon straight or branched hydrocarbon chain, and $R_x$ is hydrogen or $R_x$ and $R_y$ are each independently 1 to 4 carbon straight or branched chain alkyl, or 2 to 4 carbon straight or branched chain hydroxyalkyl; $R_{10}$ is H, or 1 to 4 carbon straight or branched chain alkyl, and $R_A$ is H or one or two groups selected from hydroxy, chloro, 1 to 4 carbon alkoxy, 2 to 8 straight or branched alkanoyloxy, 1 to 4 carbon straight or branched alkoxycarbonyloxy and dialkylamino.

Another preferred embodiment of the present invention is a compound of the formula I wherein $R_1$ is alkylene-$NR_xR_y$ where alkylene is ethylene or propylene, and $R_x$ is hydrogen or $R_x$ and $R_y$ are each independently methyl, ethyl or hydroxyethyl; $R_{10}$ is H, methyl or ethyl, and $R_A$ is H or one or two hydroxyl, chloro, methoxy, ethoxy, 2 to 8 carbon straight or branched alkanoyloxy, 1 to 4 carbon straight or branched alkoxycarbonyloxy or dimethylamino.

Still another preferred embodiment of the present invention is a compound of the formula I wherein $R_1$ is alkylene-$NR_xR_y$ where alkylene is ethylene or propylene and $R_x$ is hydrogen or $R_x$ and $R_y$ are each independently, methyl, ethyl, or hydroxyethyl; $R_{10}$ is hydrogen, and $R_A$ is hydrogen or one or two hydroxy, chloro, methoxy, trimethylacetoxy or acetoxy.

Particularly valuable are the following:

1-[[2-diethylamino)ethyl]amino]-4-nitro-9(10H)-acridinone methanesulfonate;
1-[[2-[(2-hydroxyethyl)amino]ethyl]amino]-4-nitro-9(10H)-acridinone methanesulfonate monohydrate;
1-[[2-(dimethylamino)ethyl]amino]-4-nitro-9(10H)-acridinone methanesulfonate hemihydrate;
1-[[3-(dimethylamino)propyl]amino]-4-nitro-9(10H)-acridinone methanesulfonate;
1-[[2-dimethylamino)ethyl]amino]-7-methoxy-4-nitro-9(10H)-acridinone methanesulfonate;
1-[[3-dimethylaminopropyl]amino]-7-methoxy-4-nitro-9(10H)-acridinone methanesulfonate hemihydrate;
1-[[2-(diethylamino)ethyl]amino]-7-methoxy-4-nitro-9(10H)-acridinone methanesulfonate;
1-[[2-(diethylamino)ethyl]amino]-7-hydroxy-4-nitro-9(10H)-acridinone methanesulfonate hydrate;
1-[[2-(diethylamino)ethyl]amino]-7-(dimethylamino)-4-nitro-9(10H)-acridinone methanesulfonate;
1-[[2-(diethylamino)ethyl]amino]-7-ethoxy-4-nitro-9(10H)-acridinone methanesulfonate;
1-[[2-(diethylamino)ethyl]amino]-10-methyl-4-nitro-9(10H)-acridinone methanesulfonate hydrate;
1-[[2-(dimethylamino)ethyl]amino]-7-methoxy-10-methyl-4-nitro-9(10H)-acridinone methanesulfonate;
1-[[2-(diethylamino)ethyl]amino]-7-methoxy-10-methyl-4-nitro-9(10H)-acridinone methanesulfonate;
1-[[2-(dimethylamino)ethyl]amino]-10-methyl-4-nitro-9(10H)-acridinone methanesulfonate;
1-[[3-(dimethylamino)propyl]amino]-7-methoxy-10-methyl-4-nitro-9(10H)-acridinone methanesulfonate.
1-[[2-(dimethylamino)ethyl]amino]-7-ethoxy-4-nitro-9(10H)-acridinone, methanesulfonate;
7-butoxy-1-[[2-(dimethylamino)ethyl]amino]-4-nitro-9(10H-acridinone, methanesulfonate;
7-butoxy-1-[[2-diethylamino)ethyl]amino]-4-nitro-9(10H)-acridinone, methanesulfonate;
1-[[2-(dimethylamino)-1-methylethyl]amino]-7-ethoxy-4-nitro-9(10H)-acridinone, methanesulfonate;
1-[[3-(dimethylamino)propyl]amino]-7-ethoxy-4-nitro-9(10H)-acridinone, methanesulfonate;
7-butoxy-1-[[3-(dimethylamino)propyl]amino]-4-nitro-9(10H)-acridinone, methanesulfonate;
7-ethoxy-1-[[2-[(2-hydroxyethyl)amino]ethyl]amino]-4-nitro-9(10H)-acridinone, methanesulfonate;
1-[[2-[bis(2-hydroxyethyl)amino]ethyl]amino]-7-ethoxy-4-nitro-9(10H)-acridinone, methanesulfonate;
1-[[3-(diethylamino)propyl]amino]-7-methoxy-4-nitro-9(10H)-acridinone, methanesulfonate;
1-[3-(dimethylamino)propyl]amino]-7-hydroxy-4-nitro-9(10H-acridinone, methanesulfonate;
1-[[2-(dimethylamino)-1-methylethyl]amino]-7-methoxy-4-nitro-9(10H)-acridinone, methanesulfonate;
1-[[2-(diethylamino)ethyl]amino]-4-nitro-7-propoxy-9(10H)-acridinone, methanesulfonate;
1-[[2-(dimethylamino)ethyl]amino]-7-methoxy-4-nitro-9(10H)-acridinone, N-oxide, 3-chlorobenzoate salt;
[8-[[3-(dimethylamino)propyl]amino]-9,10-dihydro-5-nitro-9-oxo-2-acridinyl]2,2-dimethylpropanoate, methane-sulfonate salt, and
1-chloro-8-[[2-(diethylamino)ethyl]amino]-2-methoxy-5-nitro-9(10H)-acridinone, methanesulfonate.

The compounds of the invention form pharmaceutically acceptable acid addition salts with both organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic, lactic, gluconic, glucuronic; sulfamic, benzoic, tartaric, pamoic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms with pharmaceutically acceptable solvents such as water, ethanol, and the like are equivalent to the unsolvated forms for the purposes of the invention.

The compounds of the present invention and of the formula I may be prepared by reacting a 1-chloro-4-nitro-acridinone

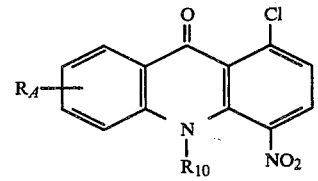

of the formula with an appropriate amine of the formula $R_1NH_2$, wherein $R_A$, $R_{10}$, and $R_1$ are as defined above, and isolating the product in free base form or pharmaceutically acceptable acid addition salt form. The reaction conditions may vary widely. The reaction may be carried out from about 2 to about 120 hours at temperatures between about 20° and 100° C. Suitable solvents are tetrahydrofuran (THF), THF-methanol, toluene, chlorobenzene, acetonitrile, 1,2-dichloroethane or chloroform.

The starting materials are known or, if new, are part of the present invention but may be prepared by known methods. For example, 1-chloro-4-nitroacridinone has been described in J. Chem. Soc., 1933, 1372; 1-chloro-4-nitroacridinones containing hydroxy, chloro, alkoxy, benzyloxy and amino substituents at the 7-position and alkyl substituents at the 10-position are described herein.

Compounds in which $R_A$ is alkanoyloxy or alkoxycarbonyloxy may be prepared from a compound of formula I in which $R_A$ is hydroxy by acylation with alkanoyl chlorides, or alkylchloroformates in the presence of a base such as triethylamine or N-ethyldiisopropylamine in an unreactive medium such as 1,2-dichloroethane.

The alkylene-$NR_xR_y$ N-oxides of formula I and as defined above may be prepared by the N-oxidation of a tertiary nitrogen by reaction with a peracid such as m-chloroperbenzoic acid in an unreactive medium such as 1,2-dichloroethane.

TEST PROTOCOLS

In Vitro

One test protocol is the in vitro proliferating human colon adenocarcinoma (HCA) cell screen. In this test, HCT-8 cells (HCA cell line received from Yale University) are trypsinized using trypsin-EDTA. A single cell suspension is achieved by passing the cells through a 26-gauge needle with a 20-cc syringe. A cell suspension is prepared using RPMI 1640+10% FCS+50 µg/ml gentamicin sulfate with a cell concentration of approximately 5,000 cells/ml. The cell suspension is dispensed in Linbro 24-well plates; 1 ml/well. The plates are incubated for approximately 48 hours at 37° C. in a 5% $CO_2$ atmosphere. At this time test compounds are added in the appropriate concentration. Ten µl of the appropriate dilution is added to each well for a titration test. The plates are reincubated an additional 60-65 hours at 37° C. in a 5% $CO_2$ atmosphere. The cells are lysed using a mix of cationic surfactant, glacial acetic acid and sodium chloride. Two ml of the lysed cell suspension from each well is added to 8 ml of diluent. The number of nuclei is determined using a Coulter counter (ZBI model), and a percent growth for each drug concentration is calculated. From this, an $ID_{50}$ (molar concentration of compound that results in 50% inhibition of growth) is determined.

Another test protocol is the in vitro antitumor screening (PDC test) of compounds of the present invention on L1210 murine leukemia cell lines. L1210 cells, a murine leukemia cell line, were grown in RPMI 1640 supplemented with 5% fetal bovine serum and gentamicin (50 µg/ml).

Drug dilutions were prepared in the apropriate solvent and 20 µl of each dilution were added to 24-well Linbro tissue culture plats, followed by the addition of M 2.0 ml of cell suspension containing $3 \times 10^4$ cells per ml. Solvent and medium controls were included in each test. After incubation at 37° C. for three days in 5% $CO_2$, the contents of each well were removed and the cells counted in a ZBI Coulter counter. Percent growth was calculated relative to the controls and the levels of drug activity wre expressed as $ID_{50}$ in moles per liter using probit paper.

Still another test protocol is the in vitro antibacterial (ABMF) test which is a recognized standard microdilution susceptibility procedure in Mueller-Hinton broth against Gram-positive and Gram-negative bacterial test organisms. The procedure is a modification of a state-of-the-art procedure reported in *Manual of Clinical Microbiology*, Lennette, E. H., ed., by Barry, A. L. and C. Thornsberry at pages 463–474 and by Gavan, T. L. and A. L. Barry at pages 459–462, American Society for Microbiology, Washington, 1980.

In the test, a given bacterial culture is used to inoculate individual test wells of microdilution trays containing growth medium and test compound, the latter in a microdilution series: 1000, 333, 111, 37, 12, 4, 1.4, and 0.46 micrograms per milliliter. The resulting inoculated trays are each sealed, incubated with blank controls at 37° C. for 16–24 hours, and then read for minimum inhibitory concentration (MIC), the lowest concentration of test compound that completely inhibits bacterial growth. MIC values lower than 333 mcg/ml indicate antimicrobial activity. For convenience, values are reported for *Escherichia coli, Corynebacterium Sp.* ATCC 21698, *Branhamella catarrhalis, Streptococcus pneumoniae,* and *Bacillus cereus.*

Another test protocol is the in vivo lymphocytic leukemia P388 test. the animals used are either male or female $CD_2F_1$ mice, six or seven animals per test group. The tumor transplant is by intraperitoneal injection of dilute ascitic fluid containing cells of lymphocytic leukemia P388. The test compounds are administered intraperitoneally once daily for five consecutive days at various doses following tumor inoculation. The animals are weighed and survivors are recorded on a regular basis for 30 days. A compound is designated "toxic" if, at a given dose, all animals die prior to four days after the first injection of drug. A ratio of survival time for treated (T)/control (C) animals is calculated. A criterion for efficacy is a ratio T/C times 100 greater than or equal to 125. See *Cancer Chemotherapy Reports,* Part 3, 3, 1 (1972) for a comprehensive discussion of the protocol.

These test protocol procedures gave results listed in the following Tables for representative compounds of the invention.

TABLE I

![Structure: substituted quinoline with HN-R1, NO2, and RA-substituted aromatic ring connected via carbonyl]

| Example No. | R_A | R_1 | Formula | mp, °C. | In Vitro ID$_{50}$ × 10$^7$ PDC | In Vitro ID$_{50}$ × 10$^7$ HCA | P388 in vivo Dose (mg/kg) | P388 in vivo T/C × 100 | ABMF minimal inhibitory conc (μ/ml) E. coli | Coryn. Species | B. cat. | S. pneu. | B. cer. |
|---|---|---|---|---|---|---|---|---|---|---|---|---|---|
| 1 | H | CH$_2$CH$_2$N(C$_2$H$_5$)$_2$ | C$_{19}$H$_{22}$N$_4$O$_3$·CH$_3$SO$_3$H | 166–168 | 4.5 | — | 50 / 25 | 172 / 145 | 12.3 | <0.46 | <0.46 | <0.46 | 12.3 |
| 2 | 7-OH | CH$_2$CH$_2$N(C$_2$H$_5$)$_2$ | C$_{19}$H$_{22}$N$_4$O$_4$·CH$_3$SO$_3$H·H$_2$O | 220–225 | 0.067 | 0.045 | 12.5 | 250 | <0.46 | <0.46 | <0.46 | <0.46 | <0.46 |
| 3 | 7-OMe | CH$_2$CH$_2$N(C$_2$H$_5$)$_2$ | C$_{20}$H$_{24}$N$_4$O$_4$·CH$_3$SO$_3$H | 206–208 | 24.0 | 11.0 | 200 / 100 / 50 / 25 / 12.5 | 296 / 237 / 178 / 151 / 126 | 111 | <0.46 | <0.46 | <0.46 | 4.1 |
| 4 | 7-OEt | CH$_2$CH$_2$N(C$_2$H$_5$)$_2$ | C$_{21}$H$_{26}$N$_4$O$_4$·CH$_3$SO$_3$H | 229–231 | 6.8 | 4.0 | 100 / 50 / 25 / 12.5 | 273 / 211 / 149 / 129 | >1000 | 4.1 | 37 | >1000 | >1000 |
| 5 | 7-OPr | CH$_2$CH$_2$N(C$_2$H$_5$)$_2$ | C$_{22}$H$_{28}$N$_4$O$_4$·CH$_3$SO$_3$H | 172–174 | — | 19.5 | 200 / 100 / 50 / 25 / 12.5 | 186 / 164 / 146 / 136 / 122 | >1000 | 0.46 | >1000 | 1000 | >1000 |
| 6 | 7-OBu | CH$_2$CH$_2$N(C$_2$H$_5$)$_2$ | C$_{23}$H$_{30}$N$_4$O$_4$·CH$_3$SO$_3$H | 189–191 | 5.8 | — | 50 / 25 | 160 / 139 | >1000 | >1000 | >1000 | >1000 | >1000 |
| 7 | 7-NMe$_2$ | CH$_2$CH$_2$N(C$_2$H$_5$)$_2$ | C$_{21}$H$_{27}$N$_5$O$_3$·CH$_3$SO$_3$H | 214–216 | 13.0 | 5.6 | 100 / 50 | 169 / 33 | >1000 | 111 | >1000 | 37 | >1000 |
| 8 | H | CH$_2$CH$_2$N(CH$_3$)$_2$ | C$_{17}$H$_{18}$N$_4$O$_3$·CH$_3$SO$_3$H·0.5H$_2$O | 216–218 | 3.9 | 3.4 | 50 / 25 | 185 / 142 | 1.4 | <0.46 | <0.46 | <0.46 | 4.1 |
| 9 | 7-OMe | CH$_2$CH$_2$N(CH$_3$)$_2$ | C$_{16}$H$_{20}$N$_4$O$_4$·CH$_3$SO$_3$H | 254–256 | 2.6 | 8.9 | 200 / 100 / 50 / 25 | 269 / 201 / 146 / 124 | >1000 | <0.46 | <0.46 | <0.46 | >1000 |
| 10 | 7-OEt | CH$_2$CH$_2$N(CH$_3$)$_2$ | C$_{19}$H$_{22}$N$_4$O$_4$·CH$_3$SO$_3$H | 273–274 | 8.1 | 3.6 | 200 / 100 / 50 / 25 | 260 / 193 / 162 / 128 | >1000 | >1000 | >1000 | >1000 | >1000 |
| 11 | 7-OBu | CH$_2$CH$_2$N(CH$_3$)$_2$ | C$_{21}$H$_{26}$N$_4$O$_4$·CH$_3$SO$_3$H | 221–223 | 16.0 | — | 50 / 25 | 175 / 130 | >1000 | 4.1 | 4.1 | >1000 | >1000 |
| 12 | 7-OMe | CH$_3$, CH$_2$CH$_2$N(CH$_3$)$_2$ | C$_{19}$H$_{22}$N$_4$O$_4$·CH$_3$SO$_3$H | 245–247 | 8.8 | 4.5 | 200 / 100 / 50 / 25 | 245 / 180 / 144 / 122 | 1.4 | 4.1 | 4.1 | <0.46 | 4.1 |

TABLE I-continued

Structure: A tricyclic compound with positions labeled 5, 6, 7, 8 on one ring bearing $R_A$ at position 6/7, carbonyl (C=O) bridge, NH ring nitrogen, with HN—$R_1$ and $NO_2$ substituents on the other ring.

| Example No. | $R_A$ | $R_1$ | Formula | mp, °C. | In Vitro ID$_{50}$ × 10$^7$ PDC | In Vitro ID$_{50}$ × 10$^7$ HCA | P388 in vivo Dose (mg/kg) | P388 in vivo T/C × 100 | ABMF minimal inhibitory conc (μ/ml) E. coli | Coryn. Species | B. cat. | S. pneu. | B. cer. |
|---|---|---|---|---|---|---|---|---|---|---|---|---|---|
| 13 | 7-OEt | CH$_3$ \| CH$_2$CH$_2$N(CH$_3$)$_2$ | C$_{20}$H$_{24}$N$_4$O$_4$·CH$_3$SO$_3$H | 180–182 | 10.9 | 5.0 | 50 / 25 | 227 / 180 | 12.3 | <0.46 | 4.1 | 1.4 | 12.3 |
| 14 | 7-OMe | O ‖ CH$_2$CH$_2$N(C$_2$H$_5$)$_2$ | C$_{18}$H$_{20}$N$_4$O$_5$·C$_7$H$_5$ClO$_2$ | 177–178 | — | — | 50 | 157 | 12.3 | 1.4 | 12.3 | <0.46 | 333 |
| 15 | H | CH$_2$CH$_2$NH$_2$ | C$_{15}$H$_{14}$N$_4$O$_3$·CH$_3$SO$_3$H·½H$_2$O | 243–246 | 13.0 | 5.2 | 50 | 128 | <0.46 | <0.46 | <0.46 | <0.46 | 1.4 |
| 16 | H | H \| CH$_2$CH$_2$NCH$_2$CH$_2$OH | C$_{17}$H$_{18}$N$_4$O$_4$·CH$_3$SO$_3$H·H$_2$O | 160–169 | 3.3 | 2.0 | 50 / 25 | 159 / 125 | 1.4 | <0.46 | <0.46 | 1.4 | 1.4 |
| 17 | 7-OEt | H \| CH$_2$CH$_2$NCH$_2$CH$_2$OH | C$_{19}$H$_{22}$N$_4$O$_5$·CH$_3$SO$_3$H | 255–256 | 1.8 | 1.2 | 50 / 25 | 138 / 124 | <0.46 | <0.46 | 1.4 | 1.4 | 4.1 |
| 18 | 7-OBu | H \| CH$_2$CH$_2$NCH$_2$CH$_2$OH | C$_{21}$H$_{26}$N$_4$O$_5$·CH$_3$SO$_3$H | 248–249 | 3.5 | 4.0 | 25 / 12.5 | 136 / 121 | 111 | 37 | 333 | 37 | 333 |
| 19 | 7-OEt | CH$_2$CH$_2$N(CH$_2$CH$_2$OH)$_2$ | C$_{21}$H$_{26}$N$_4$O$_6$·CH$_3$SO$_3$H | 232–234 | 15.0 | 10.1 | 200 / 100 | 147 / 130 | >1000 | >1000 | 111 | >1000 | >1000 |
| 20 | H | CH$_2$CH$_2$CH$_2$N(CH$_3$)$_2$ | C$_{16}$H$_{20}$N$_4$O$_3$·CH$_3$SO$_3$H | 206–208 | 5.7 | 2.0 | 100 / 50 | 189 / 144 | 1.4 | <0.46 | <0.46 | <0.46 | 4.1 |
| 21 | 7-OH | CH$_2$CH$_2$CH$_2$N(CH$_3$)$_2$ | C$_{18}$H$_{20}$N$_4$O$_4$·CH$_3$SO$_3$H | 247–249 | 0.19 | 0.028 | 6.25 / 3.12 / 1.56 | 234 / 187 / 162 | <0.46 | 0.46 | <0.46 | 0.46 | <0.46 |
| 22 | 7-OMe | CH$_2$CH$_2$CH$_2$N(CH$_3$)$_2$ | C$_{19}$H$_{22}$N$_4$O$_4$·CH$_3$SO$_3$H·0.5H$_2$O | 175–177 | 12.0 | 2.6 | 100 / 50 / 25 / 12.5 / 6.25 | 205 / 225 / 178 / 156 / 138 | 1.4 | <0.46 | <0.46 | <0.46 | 4.1 |
| 23 | 7-OEt | CH$_2$CH$_2$CH$_2$N(CH$_3$)$_2$ | C$_{20}$H$_{24}$N$_4$O$_4$·CH$_3$SO$_3$H | 211–213 | 3.2 | 2.0 | 50 / 25 / 12.5 | 210 / 157 / 135 | <0.46 | <0.46 | <0.46 | 1.4 | 12.3 |
| 24 | 7-OBu | CH$_2$CH$_2$CH$_2$N(CH$_3$)$_2$ | C$_{22}$H$_{28}$N$_4$O$_4$·CH$_3$SO$_3$H | 182–185 | 3.5 | 3.7 | 25 / 12.5 | 151 / 123 | 12.3 | 4.1 | 12.3 | 1.4 | 111 |

TABLE I-continued

[Structure: quinoline-based compound with R_A at positions 6,7, R_1 on HN group, NO_2 group, and C=O linker]

| Example No. | R_A | R_1 | Formula | mp, °C. | In Vitro ID_50 × 10^7 PDC | In Vitro ID_50 × 10^7 HCA | P388 in vivo Dose (mg/kg) | P388 in vivo T/C × 100 | ABMF minimal inhibitory, conc ($\mu$/ml) E. coli | Coryn. Species | B. cat. | S. pneu. | B. cer. |
|---|---|---|---|---|---|---|---|---|---|---|---|---|---|
| 25 | 7-OCOCMe_3 | CH_2CH_2CH_2N(CH_3)_2 | C_23H_28N_4O_5.CH_3SO_3H | 200–204 | 0.15 | — | 12.5<br>6.25<br>3.12<br>1.56 | 248<br>214<br>173<br>156 | 111 | 333 | 333 | 333 | 111 |
| 26 | 7-OMe | CH_2CH_2CH_2N(C_2H_5)_2 | C_21H_26N_4O_4.CH_3SO_3H | 204–206 | 0.78 | 2.7 | 100<br>50<br>25<br>12.5 | 198<br>161<br>142<br>127 | 12.3 | 0.46 | <0.46 | 4.1 | 12.3 |
| 27 | 7-OMe, 8-Cl | CH_2CH_2N(C_2H_5)_2 | C_20H_23ClN_4O_4.CH_3SO_3H | 202–207 | 4.2 | — | | | 4.1 | <0.46 | 1.4 | 1.4 | 4.1 |
| 28 | 6-OH | CH_2CH_2N(C_2H_5)_2 | C_19H_22N_4O_4.CH_3SO_3H | 222–226 | 3.6 | — | | | 1.4 | <0.46 | <0.46 | <0.46 | 1.4 |
| 29 | 8-OH | CH_2CH_2N(C_2H_5)_2 | C_19H_22N_4O_4.CH_3SO_3H | 235–238 | 0.88 | — | | | 1.4 | <0.46 | <0.46 | <0.46 | <0.46 |

TABLE II

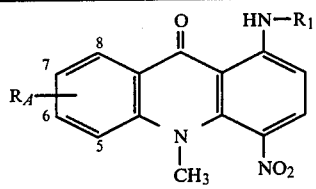

| Example No. | $R_A$ | $R_1$ | Formula | mp, °C. | In Vitro $ID_{50} \times 10^7$ PDC | In Vitro $ID_{50} \times 10^7$ HCA | P388 in vivo Dose (mg/kg) | P388 in vivo $T/C \times 100$ |
|---|---|---|---|---|---|---|---|---|
| 30 | H | $CH_2CH_2N(C_2H_5)_2$ | $C_{20}H_{24}N_4O_3 \cdot CH_3SO_3H \cdot H_2O$ | 168–169 | — | — | 200 | 147 |
| 31 | 7-OMe | $CH_2CH_2N(C_2H_5)_2$ | $C_{21}H_{26}N_4O_4 \cdot CH_3SO_3H$ | 227–230 | — | — | 200 | 128 |
|  |  |  |  |  |  |  | 100 | 128 |
| 32 | H | $CH_2CH_2N(CH_3)_2$ | $C_{18}H_{20}N_4O_3 \cdot CH_3SO_3H$ | 257–261 | 32.0 | — | 100 | 146 |
|  |  |  |  |  |  |  | 50 | 126 |
| 33 | 7-OMe | $CH_2CH_2N(CH_3)_2$ | $C_{19}H_{22}N_4O_4 \cdot CH_3SO_3H$ | 264–266 | 18.0 | 22.7 | 200 | 144 |
|  |  |  |  |  |  |  | 100 | 137 |
| 34 | 7-OMe | $CH_2CH_2CH_2N(CH_3)_2$ | $C_{20}H_{24}N_4O_4 \cdot CH_3SO_3H$ | 245–246 | 7.8 | 7.1 | 100 | 136 |
|  |  |  |  |  |  |  | 50 | 123 |

| Example No. | E. coli | Coryn. Species | B. cat. | S. pneu. | B. cer. |
|---|---|---|---|---|---|
|  | ABMF minimal inhibitory, conc (μ/ml) | | | | |
| 30 | 111 | 111 | 111 | 37 | 111 |
| 31 | >1000 | 1000 | >1000 | >1000 | >1000 |
| 32 | 37 | 333 | >1000 | 12.3 | >1000 |
| 33 |  |  |  |  |  |
| 34 | 12.3 | 12.3 | 12.3 | 12.3 | 12.3 |

When being utilized as antimicrobial and antitumor agents, the compounds of the invention can be prepared and administered in a wide variety of topical, oral, and parenteral dosage forms. It will be clear to those skilled in the art that the following dosage forms may comprise as the active component, one or more compounds of formula I, a corresponding pharmaceutically acceptable salt of any of said compounds, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet, the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Topical preparations include creams, lotions, gels, and sprays. These various topical preparations may be formulated by well-known procedures. See for example Remington's Pharmaceutical Sciences, Chapter 43, 14th Ed., Mack Publishing Co., Easton, Pa. 18042, USA.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 50 mg to 500 mg according to the particular application and the potency of the active ingredient.

In therapeutic use as antimicrobial and antitumor agents the compounds utilized in the pharmaceutical method of this invention are administered at the initial dosage of about 0.1 mg to about 50 mg per kilogram. A dose range of about 0.5 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain preservative to prevent the growth of microorganisms.

The pharmaceutical forms suitable for injectable use include sterile aqueous solutions to dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), N,N-dimethylacetamide, suitable mixtures thereof and vegetable oils. The proper fluidity can be maintained, for example, by the use of a coating such as lecithin; by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compoositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in unit dosage form for ease of administration and uniformity of dosage. Unit dosage forms used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel unit dosage forms of the invention are dictated by and directly dependent on (a) the unique characteristics of the active material and the particular therapeutic effect to be achieved, and (b) the limitation inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in unit dosage form as hereinbefore disclosed. A unit dosage form can, for example, contain the principal active compound in amounts ranging from about 0.1 to about 500 mg, with from about 0.5 to about 250 mg being preferred. Expressed in proportions, the active compound is generally present in from about 0.1 to about 500 mg/ml of carrier. In the case of compositions containing supplementary active ingredients, the dosages are determined by reference to the usual dose and the manner of administration of the said ingredients. The daily parenteral doses for mammalian subjects to be treated ranges from 0.1 mg/kg to 100 mg/kg. The preferred daily dosage range is 0.3 mg/kg to 10 mg/kg.

PREPARATIVE EXAMPLES

The invention and the best mode of practicing the same are illustrated by the following examples of preferred embodiments of selected compounds and their preparation.

EXAMPLE 1

1-[[2-(Diethylamino)ethyl]amino]-4-nitro-9-(10H)-acridinone, methanesulfonate (1:1)

To a suspension of 6.87 g (0.025 mol) of 1-chloro-4-nitro-9(10H)-acridinone in 250 ml of THF was added 6.09 (0.052 mol) of N,N-diethylethylenediamine and the mixture stirred for 19 hours at 25° C. The yellow solid (6.31 g) was collected and the filtrate concentrated to 30 ml providing a second crop (1.98 g) of the free base of the title compound, mp 194°–195° C. The title salt was obtained by combining the base with one equivalent of methanesulfonic acid in methanol and adding diethyl ether. The mp is 166°–168° C. after recrystallization from acetonitrile.

EXAMPLE 2

1-[[2-(Diethylamino)ethyl]amino]-7-hydroxy-4-nitro-9(10H)-acridinone, methanesulfonate (1:1), hydrate (1:1)

A mixture of 1.16 g (0.004 mol) of 1-chloro-7-hydroxy-4-nitro-9(10H)-acridinone, 1.16 g (0.010 mol) of N,N-diethylethylenediamine and 45 ml of THF was stirred 5.5 hours at 25° C., 1.5 hours at 50° C., 16 hours at 25° C., and filtered. The precipitate was washed with THF and then with water, and dried to provide 1.00 g of the free base. The title salt was obtained by adding ethyl acetate to a methanolic solution of equimolar amounts of free base and methanesulfonic acid, mp 220°–225° C. (decomp.), after loss of water.

1-Chloro-7-hydroxy-4-nitro-9(10H)-acridinone

To a stirred and boiling mixture of 26.7 g of 1-chloro-4-nitro-7-(phenylmethoxy)-9(10H)-acridinone in 1.9 l of glacial acetic acid was added 13.0 ml of methanesulfonic acid. Heating and stirring were continued for seven hours and the mixture was filtered. The precipitate was suspended in 250 ml of boiling glacial acetic acid, cooled to 60°, collected, washed with water and then methanol, and dried providing the title compound, mp above 325° C.

2-Chloro-5-nitro-6-[[4-(phenylmethoxy)phenyl]amino]-benzoic acid

A mixture of 50.0 g of 2,6-dichloro-3-nitrobenzoic acid, 85.7 g of 4-benzyloxyaniline, and 115 ml of N,N-dimethylaniline was heated on a steam bath for 24 hours. The cooled mixture was triturated with 600 ml of chloroform and filtered. The precipitate was stirred in a mixture of 350 ml of chloroform and 350 ml of 1N aq NaOH. The red sodium salt was collected and stirred with a mixture of 300 ml of 1N hydrochloric acid and 1.5 l of chloroform. The chloroform layer was concentrated to provide the title compound as red crystals, mp 172°–174° C.

1-Chloro-4-nitro-7-(phenylmethoxy)-9-(10H)-acridinone

Four grams of 2-chloro-5-nitro-6-[[4-(phenylmethoxy)phenyl]amino]benzoic acid was suspended in 80 ml of boiling 1,2-dichloroethane to which 0.2 ml of N,N-dimethylaniline was added followed by 8.0 ml of phosphorus oxychloride. The mixture was stirred under reflux for 30 minutes and cooled overnight. The resulting suspension was filtered providing the title compound as a red solid, mp 216°–217° C.

EXAMPLE 3

1-[[2-(Diethylamino)ethyl]amino]-7-methoxy-4-nitro-9(10H)-acridinone, methanesulfonate (1:1)

A mixture of 1.07 g (0.0035 mol) of 1-chloro-7-methoxy-4-nitro-9(10H)-acridinone, 50 ml of THF and 0.78 g (0.007 mol) of N,N-diethylethylenediamine was stirred at 25° C. for 20 hours. The orange solid was collected, washed with cold THF and then with water, and dried to 0.97 g. Recrystallization from toluene-cyclohexane gave the free base of the title compound, mp 179°–180° C. The title salt, mp 206°–208° C., was obtained from methanol containing an equivalent amount of methanesulfonic acid.

6-Chloro-2-[(4-methoxyphenyl)amino]-3-nitrobenzoic acid

To 74 g (0.60 mol) of p-anisidine stirred mechanically at 75° C. was added 35.4 g (0.15 mol) of 2,6-dichloro-3-nitrobenzoic acid [Lehmstedt and Schrader, *Berichte* 70B, 1526 (1937)] in small portions over one-half hour. The mixture was heated at 75° C. for 24 hours with stirring during the first two hours. The reaction mixture was cooled and the resulting solid mass was triturated in a mechanical blender with 300 ml of 2.4N hydrochloric acid. The solid was collected, washed with 3N hydrochloric acid, stirred in 400 ml of 0.5N sodium carbonate, and filtered. The filtrate, diluted with 250 ml of water, was gradually acidified with 4N hydrochloric acid. The precipitate was collected, washed with water, and dried to provide 38.5 g (79%) of the red title compound, mp 205°–213° C. A purified sample, from toluene, melts at 212°–215° C.

1-Chloro-7-methoxy-4-nitro-9(10H)-acridinone

A mixture of 12.9 g of 6-chloro-2[(4-methoxyphenyl)amino]-3-nitrobenzoic acid, 25 ml of chlorobenzene and 50 ml of phosphorus oxychloride was stirred and heated to reflux temperature over a period of one hour, and held under reflux for 4.5 hours. The mixture was cooled, filtered, and the filtrate concentrated to a viscous dark residue in vacuo. This residue and the precipitate collected previously were dissolved in 130 ml of acetic acid and cautiously treated with 15 ml of water with stirring. The resulting dark red solid was collected, washed with water, and dried to provide 11.5 g (95%) of the title compound, mp 262°–264° C.

EXAMPLE 4

1-[[2-(Diethylamino)ethyl]amino]-7-ethoxy-4-nitro-9(10H)-acridinone, methanesulfonate (1:1)

A suspension of 2.53 g (0.008 mol) of 1-chloro-7-ethoxy-4-nitro-9(10H)-acridinone, 1.92 g (0.016 mol) of N,N-diethylethylenediamine and 150 ml of THF was stirred 18 hours at 25° C. The crystalline yellow base (mp 188°–189° C.) was collected and converted to the title salt, mp 229°–231° C., in methanol containing one equivalent of methanesulfonic acid.

1-Chloro-7-ethoxy-4-nitro-9(10H)-acridinone

A mixture of 28.0 g (0.20 mol) of p-phenetidine, 23.6 g (0.10 mol) of 2,6-dichloro-3-nitrobenzoic acid, and 80 ml of N,N-dimethylaniline was heated five hours on a steam bath. The resulting mixture was diluted with chloroform and extracted with 1N aq. NaOH. Acidification of the aqueous extract yielded 6-chloro-2-[4-ethoxyphenyl)amino]-3-nitrobenzoic acid as reddish brown crystals, mp 174°–176° C.

Fifteen grams of the above acid together with 1.5 ml of N,N-dimethylaniline and 30 ml of phosphorus oxychloride in 200 ml of chloroform was stirred under reflux for two hours. After standing at room temperature overnight, the mixture was filtered providing the title compound as shiny black crystals, mp 224°–246° C.

EXAMPLE 5

1-[[2-(Diethylamino)ethyl]amino]-4-nitro-7-propoxy-9(10H)-acridinone, methanesulfonate A slurry of 1.5 g of 1-chloro-4-nitro-7-propoxy-9(10H)-acridinone and 1 g of N,N-diethylethylenediamine, in 150 ml of THF and 50 ml of methanol was stirred 18 hours and then concentrated to a volume of 75 ml in vacuo. The free base, mp 191.5°–193° C., crystallized which was collected by filtration, dissolved in chloroform, and treated with an equivalent of methanolic methanesulfonic acid and acetone to provide the title salt, mp 172°–174° C.

1-Chloro-4-nitro-7-propoxy-9(10H)acridinone

A mixture of 24.5 g of 4-propoxyaniline, 19.8 g of 2,6-dichloro-3-nitrobenzoic acid, and 150 ml N,N-dimethylaniline was heated under nitrogen at 100° overnight. The cooled reaction mixture was treated with dilute base and chloroform. After the aqueous layer was washed several times with chloroform, it was treated with hydrochloric acid and the resulting orange needles were collected by filtration and washed with water to give 6-chloro-3-nitro-2-[(4-propoxyphenyl)amino]benzoic acid, mp 194°–196° C.

A mixture of 21.05 g of the above acid, 1 ml of N,N-dimethylaniline, 42 ml of phosphorus oxychloride, and 200 ml of 1,2-dichloroethane was heated at reflux 30 minutes. The reaction mixture was cooled to room temperature and the resulting red solid was collected by filtration and washed with chloroform to provide the title compound, mp 174°–175° C.

EXAMPLE 6

7-Butoxy-1-[[2-(diethylamino)ethyl]amino]-4-nitro-9-(10H)-acridinone, methanesulfonate A slurry of 2.1 g of 7-butoxy-1-chloro-4-nitro-9(10H)acridinone and 1.37 g N,N-diethylethylenediamine in 50 ml of THF was stirred at room temperature 18 hours and filtered to collect the resulting yellow cottony needles which were washed with water to provide the free base, mp 192°–193° C. Treatment of a dichloromethane solution of the base with an equivalent of methanolic methanesulfonic acid provided the title salt, mp 189°–191° C.

7-Butoxy-1-chloro-4-nitro-9(10H)acridinone

A solution of 25 g of p-butoxyaniline and 17.85 g of 2,6-dichloro-3-nitrobenzoic acid in 50 ml of N,N-dimethylaniline was heated under nitrogen at 100° for 18 hours. The reaction mixture was treated with 500 ml of 0.2N sodium hydroxide and 500 ml of chloroform. The aqueous layer was washed with additional chloroform and acidified to provide 2-[(4-butoxyphenyl)amino]-6-chloro-3-nitrobenzoic acid, mp 166°–169° C.

A mixture of 17.9 g of the above acid, 45 ml of phosphorus oxychloride, 3 ml of N,N-dimethylaniline, and 500 ml of chloroform was heated at reflux for two hours and then cooled in ice. The resulting red solid was collected by filtration and washed with cold chloroform to provide the title compound, mp 154°–155° C.

EXAMPLE 7

1-[[2-(Diethylamino)ethyl]amino]-7-(dimethylamino)-4-nitro-9(10H)-acridinone, methanesulfonate (1:1)

A mixture of 1.59 g (0.005 mol) of 1-chloro-7-(dimethylamino)-4-nitro-9(10H)-acridinone, 1.30 g (0.011 mol) of N,N-diethylethylenediamine and 50 ml of THF was stirred for six hours at 25° C. The mixture was evaporated to dryness. The residue was washed with water, dissolved in chloroform and washed with dilute aqueous Na$_2$CO$_3$, dried, and evaporated to 1.91 g of the title compound free base. The title salt, mp 214°–216° C. was obtained from methanol-ethyl acetate containing equivalent amounts of the base and methanesulfonic acid.

1-Chloro-7-(dimethylamino)-4-nitro-9(10H)acridinone

A mixture of 41.0 g of N,N-dimethyl-p-phenylenediamine, 100 ml of N,N-dimethylaniline, and 23.6 g of 2,6-dichloro-3-nitrobenzoic acid was heated for seven hours on a steam bath. The resulting cake was suspended in dichloromethane, filtered, and the solid washed with water. Recrystallization from DMF-ethanol provided 6-chloro-2[[4-(dimethylamino)phenyl]amino]-3-nitrobenzoic acid, mp 222°–223° C. (dec).

To a solution of 8.40 g of the above acid in 300 ml of 1,2-dichloroethane and 19.0 ml of triethylamine was added 4.2 ml of phosphorus oxychloride, the mixture stirred for two hours, and treated with 10.0 ml of methanol. This mixture was concentrated under reduced pressure to a residue which was triturated with 80 ml of methanol. The solid was collected, triturated with aqueous ammonia, dried, and recrystallized from DMF providing the title compound, mp above 300° C., as a black solid.

EXAMPLE 8

1-[[2-(Dimethylamino)ethyl]amino]-4-nitro-9(10H)-acridinone, methanesulfonate (1:1), hemihydrate A mixture of 6.87 g (0.025 mol) of 1-chloro-4-nitro-9(10H)-acridinone, 250 ml of THF, and 4.84 g (0.055 mol) of N,N-dimethylethylenediamine was stirred at 25° C. for 2.5 hours. The precipitate was collected, washed with THF and then with water, and dried to 7.24 g of the yellow free base, mp 212°–213° C. The title compound, mp 216°–218° C., was obtained from an aqueous methanolic solution of the base and one equivalent of methanesulfonic acid.

EXAMPLE 9

1-[[2-(Dimethylamino)ethyl]amino]-7-methoxy-4-nitro-9(10H)-acridinone, methanesulfonate (1:1)

A dark red suspension of 4.57 g (0.015 mol) of 1-chloro-7-methoxy-4-nitro-9(10H)-acridinone and 2.8 g (0.032 mol) of N,N-dimethylethylenediamine in 150 ml of THF was stirred at 25° C. for 5.5 hours. The orange precipitate was collected, washed with THF and then with water, and dried to 5.15 g of title compound free base, mp 234°–237° C. The methanesulfonate salt crystallized from an aqueous methanolic solution of equivalent amounts of the base and methanesulfonic acid, mp 254°–256° C. (dec.)

EXAMPLE 10

1-[[2-(Dimethylamino)ethyl]amino]-7-ethoxy-4-nitro-9(10H)-acridinone, methanesulfonate (1:1)

A suspension of 2.53 g of 1-chloro-7-ethoxy-4-nitro-9(10H)-acridinone, 1.51 g of N,N-dimethylethylenediamine and 150 ml of THF was stirred 16 hours at 25° C. The yellow base was converted to the title salt, mp 273°–274° C. in methanol containing one equivalent of methanesulfonic acid.

EXAMPLE 11

7-Butoxy-1-[[2-(dimethylamino)ethyl]amino]-4-nitro-9(10H)-acridinone, methanesulfonate A slurry of 2.1 g of 7-butoxy-1-chloro-4-nitro-9(10H)acridinone and 1.04 g of N,N-dimethylethylenediamine in 50 ml of THF was stirred one hour and filtered. The filter cake was washed with water and dried to provide the free base, mp 194°–195° C.

Treatment of a dichloromethane-ethyl acetate solution of the base with an equivalent of methanolic methanesulfonic acid provided the title salt, mp 221°–223° C.

1-[[2-Dimethylamino)-1-methylethyl]amino]-7-methoxy-4-nitro-9(10H)-acridinone, methanesulfonate, 1.25 hydrate A slurry of 2 g of 1-chloro-7-methoxy-4-nitro-9(10/)acridinone in 175 ml of THF was treated with 2.8 g of N$^1$,N$^1$-dimethyl-1,2-propanediamine and stirred at room temperature for three days and filtered. The filter cake was washed thoroughly with methanol and dried to provide the free base, mp 176°–178° C. Treatment of a chloroform-acetone solution of the free base with an equivalent of methanolic methanesulfonic acid provided the title salt, mp 245.5°–247° C.

EXAMPLE 13

1[[2-(Dimethylamino)-1-methylethyl]amino]-7-ethoxy-4-nitro-9(10H)-acridinone, monomethanesulfonate, hyrate A mixture of 2 g of 1-chloro-7-ethoxy-4-nitro-9(10H)-acridinone and 1.28 g of $N^1,N^1$-dimethylamino-1,2-propanediamine in 150 ml of THF was stirred 18 hours and the concentrated in vacuo to an orange solid. The solid was dissolved in chloroform, washed successively with water and dilute base, dried over magnesium sulfate, and concentrated in vacuo to a solid. Trituration with methanol provided the free base, mp 149°–153° C.

Treatment of a THF solution of the base with an equivalent of methanolic methanesulfonic acid provided the title salt, mp 179.5°–182° C.

EXAMPLE 14

1-[[2-(Dimethylamino)ethyl]amino]-7-methoxy-4-nitro-9(10H)-acridinone, $N^\omega$-oxide, 3-chlorobenzoate salt A solution of 1.5 g of 1-[[2-(dimethylamino)ethyl]amino]-7-methoxy-4-nitro-9(10H)-acridinone in 150 ml of chloroform was treated with 1.03 g of 3-chloroperbenzoic acid and stirred two hours. The resulting salt was collected by filtration and was washed with chloroform to provide the title compound, mp 177°–178° C.

EXAMPLE 15

1-[(2-Aminoethyl)amino]-4-nitro-9(10H)-acridinone, methanesulfonate (1:1), hydrate (3:1)

A suspension of 3.57 g (0.013 mol) of 1-chloro-4-nitro-9(10H)-acridinone, 1.65 g (0.0275 mol) of ethylene diamine, and 75 ml of THF was stirred at 25° C. for three hours and let stand overnight. The yellow precipitate was suspended in dilute aqueous $Na_2CO_3$ and extracted with five 250 ml portions of chloroform which were combined, dried, and evaporated to a 2.8 g residue which was recrystallized from DMF providing the title free base, mp 205°–207° C. The title salt crystallized from aqueous methanol containing equimolar amounts of the base and methanesulfonic acid, mp 243°–246° C. (decomp.)

EXAMPLE 16

1-[[2-[(2-hydroxyethyl)amino]ethyl]amino]-4-nitro-9(10H)-acridinone, methanesulfonate (1:1), hydrate (1:1)

To a suspension of 0.82 g (0.003 mol) of 1-chloro-4-nitro-9(10H)-acridinone in 20 ml of THF was added a solution of 1.82 g (0.0175 mol) of 2-(2-aminoethylamino)ethanol in 20 ml of methanol, and the mixture was stirred at 25° for 17 hours. The yellow precipitate was collected, warmed in 10 ml of DMF and 1.0 ml of triethylamine until homogeneous, and diluted with 10 ml of 95% ethyl alchohol. The resulting precipitate of the free base of the title compound (mp 178°–180° C.) was converted to the title salt by crystallization from an aqueous methanolic solution containing one equivalent of methanesulfonic acid, mp 160°–169° C. (after loss of $H_2O$).

EXAMPLE 17

7-Ethoxy-1-[[2-[(2-hydroxyethyl)amino]ethyl]amino]-4-nitro-9(10H)-acridinone, methanesulfonate A slurry of 2.5 g of 1-chloro-7-ethoxy-4-nitro-9(10H)-acridinone in 150 ml of THF was treated with 4.08 g of 2-(2-aminoethylamino)ethanol in 50 ml of methanol and was stirred 18 hours. The resulting yellow solid was collected by filtration and washed with THF to provide the free base, mp 194°–195° C. A warm DMF-chloroform solution of the base was treated with an equivalent of methanolic methanesulfonic acid to provide the title salt, mp 255°–256° C.

EXAMPLE 18

7-Butoxy-1-[[2-[(2-hydroxyethyl)amino]ethyl]amino]-4-nitro-9(10H)-acridinone, methanesulfonate, 0.3 hydrate A solution of 2 g of 7-butoxy-1-chloro-4-nitro-9(10H)acridinone in 200 ml of THF was treated with 3 g of 2-(2-aminoethylamino)ethanol in 20 ml of methanol and the resulting solid was collected by filtration after stirring two hours. Washing the solid with methanol provided the free base, mp 181.5°–183° C. Treatment of a chloroform slurry of the base with methanolic methanesulfonic acid provided the title salt, mp 248°–249° C.

EXAMPLE 19

1-[[2-Bis(2-hydroxyethyl)amino]ethyl]amino]-7-ethoxy-4-nitro-9(10H)-acridinone, methanesulfonate 0.8 hydrate A slurry of 2 g of 1-chloro-7-ethoxy-4-nitro-9(10H)acridinone in 150 ml of THF was treated with 1.92 g of N,N-bis(2-hydroxyethyl)ethanediamine in 50 ml of methanol and stirred for two hours. The reaction mixture was filtered and the resulting filter cake washed with methanol and dried to provide the free base, mp 190°–193° C. Treatment of a chloroform solution of the base with an equivalent of methanolic methanesulfonic acid afforded the title salt, mp 232°–234° C.

EXAMPLE 20

1-[[3-(Dimethylamino)propyl]amino]-4-nitro-9(10H)-acridinone, methanesulfonate (1:1)

A mixture of 6.87 g (0.025 mol) of 1-chloro-4-nitro-9(10H)-acridinone, 250 ml of THF, and 5.61 g (0.055) of N,N-dimethyl-1,3-propanediamine was stirred for 2.5 hours at 25° C., and filtered. The filtrate was evaporated under reduced pressure to a pasty suspension and 100 ml of water was added with swirling. The yellow solid was collected, washed with water, dried, and recrystallized from a mixture of chloroform and cyclohexane providing the free base of the title compound, mp 146°–147° C. The 1:1 salt with methanesulfonic acid crystallized from methanol-ether-ethyl acetate, mp 206°–208° C.

EXAMPLE 21

1-[[3-Dimethylamino)propyl]amino]-7-hydroxy-4-nitro-9(10H)-acridinone, methanesulfonate (salt) (1:1)

A mixture of 2.91 g of 1-chloro-7-hydroxy-4-nitro-9(10H)-acridinone, 75 ml of THF, and 2.24 g of N,N-dimethyl-1,3-propanediamine was stirred 20 hours at 50° C. Methanol (25 ml) was added and stirring was continued at 65° C. for 20 hours. The orange solid was collected, suspended in 125 ml of water at 65° C. and aqueous sodium bicarbonate was added to bring the pH to 7. The free base of the title compound was collected, mp 212°-213° C. dec.

The title salt, mp 247°-249° C., crystallized from a solution of the free base in methanolic ethyl acetate containing an equivalent of methanesulfonic acid.

EXAMPLE 22

1-[[3-(Dimethylaminopropyl)amino]-7-methoxy-4-nitro-9(10H)-acridinone, methanesulfonate (1:1), hemihydrate To a suspension of 1.22 g (0.004 mol) of 1-chloro-7-methoxy-4-nitro-9(10H)-acridone in 50 ml of THF was added 0.92 g (0.009 mol) of N,N-dimethyl-1,3-propanediamine and the mixture stirred 18 hours at 25° C. The mixture was cooled in ice, the precipitate collected, washed with THF and then with water, and dried to 0.97 g of the free base of the title compound. The original filtrate was evaporated to a residue which was triturated with 100 ml of warm water and 0.47 g additional base was collected. The combined crops were converted to the title salt, mp 175°-177° C., in methanol containing one equivalent of methanesulfonic acid and ethyl acetate.

EXAMPLE 23

1-[[(Dimethylamino)propyl]amino]-7-ethoxy-4-nitro-9(10H)acridinone, methanesulfonate A mixture of 2 g of 1-chloro-7-ethoxy-4-nitro-9(10H)-acridinone, 1.28 g N,N,-dimethyl-1,3-propanediamine, and 150 ml of THF was stirred 18 hours and the resulting solution was reduced in vacuo to a solid. The residue was dissolved in chloroform, washed successively with water, dilute base, and water, dried, and concentrated in vacuo to provide the free base, mp 162°-162° C. Treatment of a warm THF solution of the base with methanol and an equivalent of methanolic methane sulfonic acid provided the title salt, mp 211°-213° C.

EXAMPLE 24

7-Butoxy-1-[[3-(dimethylamino)propyl]amino]-4-nitro-9(10H)-acridinone, methanesulfonate A slurry of 2 g of 7-butoxy-1-chloro-4-nitro-9(10H)acridinone in 100 ml THF was treated with 1.15 g of N,N-dimethyl-1,3-propanediamine in 50 ml of methanol and was stirred overnight.

After the solvents were removed in vacuo, the residue was dissolved in chloroform, washed with water and dilute base, dried, and concentrated in vacuo to provide the free base, mp 155°-156° C. Treatment of a warm THF solution of the base with an equivalent of methanolic methanesulfonic acid provided the title slat, mp 182°-185° C.

EXAMPLE 25

[8-[[3-(Dimethylamino)propyl]amino]-9,10-dihydro-5-nitro-9-oxo-2-acridinyl]-2,2-dimethylpropanoate, methanesulfonate (1:1), hemihydrate A mixture of 0.89 g of 1-[[3-(dimethylamino)propyl]amino]-7-hydroxy-4-nitro-9(10H)acridinone, 1.23 ml of trimethylacetyl chloride, 1.94 ml of N,N-diisopropylethylamine, and 20 ml of 1,2-dichloroethane was stirred at 80° C. for two hours. The resulting mixture was evaporated to dryness and shaken with chloroform and 5% aqueous sodium bicarbonate. The organic layer was concentrated and chromatographed over silica gel, using chloroform containing 0 to 4% added methanol. Evaporation of the desired fraction provided the desired ester free base which was converted to the title salt, mp 200°-204° C., in methanolic ethyl acetate containing one equivalent of methanesulfonic acid.

EXAMPLE 26

1-[[3-(Diethylamino)propyl]amino]-7-methoxy-4-nitro-9(10H)-acridinone, methanesulfonate (salt) (1:1)

A mixture of 3.05 g of 1-chloro-7-methoxy-4-nitro-9(10H)-acridinone and 2.86 g of N,N-diethyl-1,3-propanediamine in 50 ml of THF was stirred 17 hours at room temperature. The precipitate was collected and chromatographed over 50 g of silica gel using chloroform-methane (50:1), and crystallized from chloloroform-ethanol, providing the free base of the title compound, mp 151°-152° C.

The title salt, mp 204°-206° C., crystallized from a solution of the free base in methanolic ethyl acetate containing an equivalent of methanesulfonic acid.

EXAMPLE 27

1-Chloro-8-[[2-Diethylamino)ethyl]amino]-2-methoxy-5-nitro-9(10H)acridinone, methanesulfonate A mixture of 0.62 g 1,8-dichloro-2-methoxy-5-nitro-9(10H) acridinone and 0.5 g of N,N-diethylethanediamine was stirred in 100 ml of THF for four hours.

After the THF was removed in vacuo, the residue was triturated in methanol to provide the free base, mp 168°-171° . A chloroform solution was treated with ethanolic methanesulfonic acid to provide the title salt, mp 202°-207° C.

1,6-Dichloro-7-methoxy-4-nitro-9(10H)acridinone and 1,8-dichloro-2-methoxy-5-nitro-9(10H)acridinone A mixture of 30 g of 3-chloro-4-methoxyaniline, 18.9 g of 2,6-dichloro-3-nitrobenzoic acid, and 150 ml N,N-dimethylaniline was heated at 100° under nitrogen for 24 hours. The reaction mixture was dissolved in chloroform and washed with dilute ammonium hydroxide. After the aqueous layer was washed with chloroform, it was acidified and the resulting orange solid was collected to provide 6-chloro-2[(3-chloro-4-methoxyphenyl)amino]-3-nitrobenzoic acid, mp 222°-228° C.

A mixture of 17 g of 6-chloro-2-[(3-chloro-4-methoxyphenyl)amino]-3-nitrobenzoic acid, 35 ml of phosphorus oxychloride, 1 ml of N,N-dimethylaniline and 150 ml 1,2-dichloroethane was heated under reflux for 45 minutes. The resulting solid was collected by filtration from the hot reaction mixture and was washed with chloroform to provide 1,6-dichloro-7-methoxy-4-nitro-9(10H)-acridinone, mp 284°-285° C.

From the cooled filtrate, another solid was obtained which was chromatographed over silica gel with dichloromethane to provide 1,8-dichloro-2-methoxy-5-nitro-9(10H)acridinone, mp 251°-253° C.

EXAMPLE 28

1-[[2-(Diethylamino)ethyl]amino]-6-hydroxy-4-nitro-9(10H)acridinone, methanesulfonate (1:1)

A mixture of 1.5 g of 1-chloro-6-hydroxy-4-nitro-9(10H)-acridinone in 150 ml of THF was treated with 1.6 g N,N-diethylethylenediamine and stirred 18 hours at room temperature. The solution was concentrated in vacuo to a solid which was triturated in methanol to provide the free base as a bright yellow solid, mp 257°-258° C. This material was stirred in methanol and methanolic methanesulfonic acid to provide the title salt, mp 222°–226° C.

6-Chloro-3-nitro-2-[[3-(phenylmethoxy)phenyl]amino]-benzoid acid

A mixture of 40 g of 3-(phenylmethoxy)aniline, 47.2 g of 2,6-dichloro-3-nitrobenzoic acid, 36.8 ml of N,N-diisopropylethylamine and 160 ml of N,N-dimethylaniline was heated under nitrogen at 100° C. for three days. The cooled reaction mixture was treated with 200 ml of 10% aqueous potassium hydroxide and stirred for one hour. The resulting salt was collected by filtration, washed with chloroform and water, and then was stirred in 10% hydrochloric acid to provide the title compound, mp 155°–157° C.

1-Chloro-4-nitro-6-(phenylmethoxy)-9(10H)-acridinone and 1-chloro-8-hydroxy-4-nitro-9(10H)-acridinone A mixture of 32 g of the above acid, 60 ml of phosphorus oxychloride, 3 ml of N,N-dimethylaniline, and 300 ml of 1,2-dichloroethane was heated under reflux for 1.5 hours and then cooled. Yellow needles were collected by filtration and washed with 1,2-dichloroethane thoroughly to provide 1-chloro-4-nitro-6-(phenylmethoxy)-9(10H)-acridinone, mp 198°–202° C. The filtrate was concentrated to a gummy residue which was treated with hot glacial acetic acid and then water. The resulting reddish-brown solid was collected by filtration, dried, and then dissolved in 1 l of hot chloroform. Upon cooling, additional 1-chloro-4-nitro-6-(phenylmethoxy)-9(10H)-acridinone crystallized, mp 200°–202° C., and was collected by filtration. The concentrated filtrate was chromatographed over silica gel and eluted with dichloromethane to provide 1-chloro-8-hydroxy-4-nitro-9(10H)-acridinone, mp 265°–267° C. Elution with choloroform provided 1-chloro-4-nitro-6-(phenylmethoxy)-9(10e,uns/H/ )-acridinone, mp 207°–209° C.

1-Chloro-6-hydroxy-4-nitro-9(10H)-acridinone

A slurry of 9 g of 1-chloro-4-nitro-6(phenylmethoxy)-9(10H)-acridinone in 500 ml of 1,2-dichloroethane was treated with 30 ml of 1.0N boron tribromide in dichloromethane and then heated under reflux for two hours. Methanol was added very carefully to the hot reaction mixture until the evolution of gas ceased. Upon cooling, a yellow solid formed which was collected by filtration and washed with methanol to provide the title compound, mp 292°–294° C.

EXAMPLE 29

1-[[2-(Diethylamino)ethyl]amino]-8-hydroxy-4-nitro-9-(10H)-acridinone, methanesulfonate A slurry of 0.5 g of 1-chloro-8-hydroxy-4-nitro-9(10H)-acridinone in 75 ml of THF was treated with 0.78 g of N,N-diethylethylenediamine and stirred three hours. The resulting solution was concentrated in vacuo and the residue was dissolved in chloroform and was treated with 2-propanolic methanesulfonic acid to provide the title salt, mp 235°–238° C.

EXAMPLE 30

1-[[2-(Diethylamino)ethyl]amino]-10-methyl-4-nitro-9(10H)-acridinone, methanesulfonate (1:1), hydrate (1:1)

A mixture of 0.58 g (0.002 mol) of 1-chloro-10-methyl-4-nitro-9(10H)-acridinone, 0.50 g (0.0043 mol) of N,N-diethylethylenediamine and 25 ml of THF was stirred 24 hours at 25° C. Additional amine (0.50 g) was added and the mixture was allowed to stand at room temperature for five days. The yellow solution was evaporated to provide a residue which was dissolved in chloroform, washed with dilute aqueous NaOH, and dried. The solvent was removed in vacuo and the reside recrystallized from 95% ethanol providing the title compound free base, mp 131°–132° C. The title salt, mp 168°–169° C., crystallized from a methanolic ether solution of the base and one equivalent of methanesulfonic acid.

1-Chloro-10-methyl-4-nitro-9(10H)-acridinone

A mixture of 8.24 g (0.03 mol) of 1-chloro-4-nitro(10H)-acridinone, 50 ml of DMF, and 1.8 g of a 57% dispersion of sodium hydride in mineral oil was stirred one-half hour at room temperature, and treated with 3.0 ml of methyl iodide. Stirring was continued for 17 hours and 1.0 ml more of methyl iodide was added. At 22 hours, 0.1 g more of the sodium hydride dispersion was added, and at 24 hours, 1.0 ml more methyl iodide, and this mixture was stirred 16 hours longer. The resulting dark red mixture was cooled to 0° C., the precipitate collected, washed with a little cold DMF and then with hexane, and triturated in 200 ml of water. The aqueous suspension was filtered and the precipitate dried at 5.76 g (66%) of the title compound, mp 188°–190° C.

In the same manner, 7.62 g (0.025 mol) of 1-chloro-7-methoxy-4-nitro-9(10H)-acridinone was converted to 5.05 g (63%) of 1-chloro-7-methoxy 10-methyl-4-nitro-9(10H)-acridinone, mp 235°–240° C. after recrystallization from toluene.

EXAMPLE 31

1-[[2-(Diethylamino)ethyl]amino]-7-methoxy-10-methyl-4-nitro-9(10H)-acridinone, methanesulfonate (1:1)

A mixture of 0.96 g (0.003 mol) of 1-chloro-7-methoxy-10-methyl-4-nitro-9(10H)-acridinone, 0.87 g (0.0075 mol) of N,N-diethylethylenediamine and 30 ml of THF was stirred four hours at 50°–55° C. The clear yellow solution was evapoarated to a residue which was triturated with water and chromatographed over 30 g of silica gel in chloroform. The desired fractions were evaporated to a yellow solid (0.94 g), and converted to the title salt in methanol-water-ether containing an equivalent of methanesulfonic acid, mp 227°–230° C. with decomposition.

EXAMPLE 32

1-[[2-(Dimethylamino)ethyl]amino]-10-methyl-4-nitro-9(10H)-acridinone, methanesulfonate (1:1)

A mixture of 1.15 g (0.004 mol) of 1-chloro-10-methyl-4-nitro-9(10H)-acridinone, and 0.88 g (0.010 mol) of N,N-dimethylethylenediamine in 40 ml of THF-methanol (1:1) was stirred 16 hours at 40° C. and six hours at 50°–60° C. The yellow precipitate was collected (0.6 g, mp 179°–181° C.) and the filtrate evaporated to dryness. This residue, after trituration in water, gave 0.7 g of the same yellow free base. The title salt crystallized from aqueous methanol containing equimolar amounts of the base and methanesulfonic acid, mp 257°–261° C. with decomposition.

EXAMPLE 33

1-[[2-Dimethylamino)ethyl]amino]-7-methoxy-10-methyl-4-nitro-9(10H)-acridinone, methanesulfonate (1:1)

A mixture of 0.96 g (0.003 mol) of 1-chloro-7-methoxy-10-methyl-4-nitro-9(10H)-acridinone, 0.65 g (0.0074 mol) of N,N-dimethylethylenediamine and 30 ml of THF was stirred three hours at 50° C. and refrigerated overnight. The yellow solid was collected, washed with THF and water, and dried, mp 106°–108° C. The title salt was obtained from an aqueous methanolic solution of the base and one equivalent of methanesulfonic acid, mp 264°–266° C. with decomposition.

EXAMPLE 34

1-[[3-(Dimethylamino)propyl]amino]-7-methoxy-10-methyl-4-nitro-9(10H)-acridinone, methanesulfonate (1:1)

A combination of 1.60 g (0.005 mol) of 1-chloro-7-methoxy-10-methyl-4-nitro-9(10H)-acridinone, 1.30 g (0.0127 mol) of N,N-dimethyl-1,3-propanediamine was stirred 24 hours at 25° C., and filtered. The filtrate was evaporated to dryness and the residue triturated in water. The yellow free base was collected and dissolved in warm aqueous methanol containing an equivalent of methanesulfonic acid to crystallize the title salt, mp 245°–246° C. with decomposition.

I claim:

1. A compound of the formula

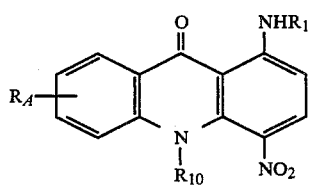

where $R_1$ is alkylene-$NR_xR_y$ where alkylene is a 2 to 4 carbon straight or branched hydrocarbon chain, which may be substituted by hydroxyl, and $R_x$ is hydrogen or $R_x$ and $R_y$ are each independently 1 to 4 carbon straight or branched chain alkyl, or 2 to 4 carbon straight or branched chain hydroxyalkyl, or alkylene-$NR_xR_y$ N-oxide where alkylene is a 2 to 4 carbon straight or branched hydrocarbon chain, and $R_x$ and $R_y$ are each independently 1 to 4 carbon straight or branched alkyl; $R_{10}$ is H or 1 to 4 carbon straight or branched chain alkyl; $R_A$ is H or one or two groups selected from hydroxy, chloro, 1 to 4 carbon alkoxy, benzyloxy, 2 to 8 carbon straight or branched alkanoyloxy, 1–4 carbon straight or branched, alkoxycarbonyloxy, amino and 1 to 4 carbon monoalkyl- or dialkylamino, or a pharmaceutically acceptable acid addition salt or a mixture thereof.

2. A compound as claimed in claim 1, wherein $R_1$ is alkylene-$NR_xR_y$ where alkylene is a 2 to 4 carbon straight or branched hydrocarbon chain, and $R_x$ is hydrogen or $R_x$ and $R_y$ are each independently 1 to 4 carbon straight or branched chain alkyl or 2 to 4 carbon straight or branched chain hydroxyalkyl; $R_{10}$ is H or 1 to 4 carbon straight or branched alkyl, and $R_A$ is H or one or two groups selected from hydroxy, chloro, 1 to 4 carbon alkoxy, 2 to 8 carbon straight or branched alkanoyloxy, 1 to 4 carbon straight or branched alkoxycarbonyloxy and 2 to 4 carbon dialkylamino.

3. A compound as claimed in claim 2, wherein $R_1$ is alkylene-$NR_xR_y$ where alkylene is ethylene or propylene, and $R_x$ is hydrogen or $R_x$ and $R_y$ are each independently methyl, ethyl, or hydroxyethyl; $R_{10}$ is H, methyl or ethyl, and $R_A$ is H or one or two groups selected from hydroxy, chloro, methoxy, ethoxy, 2 to 8 carbon straight or branched alkanoyloxy, 1 to 4 carbon straight or branched alkoxycarbonyloxy and dimethylamino.

4. A compound as claimed in claim 3, wherein $R_1$ is alkylene-$NR_xR_y$ where alkylene is ethylene or propylene and $R_x$ is hydrogen or $R_x$ and $R_y$ are each independently methyl, ethyl, or hydroxyethyl; $R_{10}$ is hydrogen, and $R_A$ is hydrogen or one or two groups selected from hydroxy, chloro, methoxy, trimethylacetoxy and acetoxy.

5. A compound as claimed in claim 4 and being 1-[[2-(dimethylamino)ethyl]amino]-7-methoxy-4-nitro-9(10H)-acridinone methanesulfonate.

6. A compound as claimed in claim 4 and being 1-[[3-(dimethylaminopropyl)]amino]-7-methoxy-4-nitro-9(10H)-acridinone methanesulfonate hemihydrate.

7. A compound as claimed in claim 4 and being 1-[[2-(diethylamino)ethyl]amino]-7-methoxy-4-nitro-9(10H)-acridinone methanesulfonate.

8. A compound as claimed in claim 4 and being 1-[[2-(diethylamino)-ethyl]amino]-7-hydroxy-4-nitro-9(10H)-acridinone methanesulfonate monohydrate.

9. A compound as claimed in claim 3 and being 1-[[2-(diethylamino)ethyl]-amino]-7-ethoxy-4-nitro-9(10H)-acridinone methanesulfonate.

10. A compound as claimed in claim 3 and being 1-[[2-(dimethylamino)ethyl]amino]-7-ethoxy-4-nitro-9(10H)acridinone methanesulfonate.

11. A compound as claimed in claim 4 and being 1-[[3-(dimethylamino)propyl]amino-7-hydroxy-4-nitro-9(10H)-acridinone methanesulfonate.

12. A compound as claimed in claim 2 and being 1-[[2-dimethylamino)-1-methylethyl]amino]-7-methoxy-4-nitro-9(10H)-acridinone methanesulfonate.

13. A compound as claimed in claim 4 and being [8-[[3-(dimethylamino)]propyl]amino]-9,10-dihydro-5-nitro-9-oxo-2-acridinyl ester methanesulfonate 2,2-dimethylpropanoic acid.

14. A pharmaceutical composition comprising a therapeutically effective amount of a compound as claimed in claim 1 together with a pharmaceutically acceptable carrier.

15. A method for treating bacterial infections in a mammal comprising administering an effective amount of a pharmaceutical composition as claimed in claim 14 to such mammal in need thereof.

16. A method for treating leukemia in a mammal comprising administering an effective amount of a pharmaceutical composition as claimed in claim 14 to such mammal in need thereof.

* * * * *